United States Patent [19]

Inaoka et al.

[11] Patent Number: 5,556,835

[45] Date of Patent: Sep. 17, 1996

[54] GEL-LIKE FRAGRANCE COMPOSITION

[75] Inventors: Toru Inaoka, Hyogo; Hideyuki Tahara, Osaka; Masahiko Shinohara, Chiba, all of Japan

[73] Assignees: Nippon Shokubai Co., Ltd., Osaka; Nihon Firmenich Kabushiki Kaisha, Tokyo, both of Japan

[21] Appl. No.: 269,137

[22] Filed: Jun. 30, 1994

[30] Foreign Application Priority Data

Jul. 2, 1993 [JP] Japan .................................. 5-164653

[51] Int. Cl.$^6$ ...................................................... A61K 7/46
[52] U.S. Cl. ...................................................... 512/3; 512/4
[58] Field of Search .................................................. 512/3, 4

[56] References Cited

U.S. PATENT DOCUMENTS

| | | | |
|---|---|---|---|
| 3,994,439 | 11/1976 | Van Breen et al. | 512/4 |
| 4,117,110 | 9/1978 | Hautmann | 424/76 |
| 4,362,841 | 12/1982 | Minatono et al. | 524/531 |
| 4,492,644 | 1/1985 | Matsumoto et al. | 512/4 |
| 4,582,635 | 4/1985 | Furuichi et al. | 512/4 |
| 4,587,129 | 5/1986 | Kliment | 512/4 |
| 4,842,761 | 6/1989 | Rutherford | 512/4 |
| 5,034,222 | 7/1991 | Kellett et al. | 424/76.4 |

FOREIGN PATENT DOCUMENTS

| | | |
|---|---|---|
| 0152982 | 8/1985 | European Pat. Off. . |
| 0441512A2 | 8/1991 | European Pat. Off. . |
| 54-135229 | 10/1979 | Japan . |
| 55-81655 | 6/1980 | Japan . |
| 59-77859 | 5/1984 | Japan . |
| 5-15777 | 1/1993 | Japan . |

*Primary Examiner*—James H. Reamer
*Attorney, Agent, or Firm*—Burns, Doane, Swecker & Mathis, LLP

[57] ABSTRACT

Gel-like fragrance composition which comprises an aqueous gel comprising an aqueous fluid and a gelling agent incorporated an oil-absorbable resin carrying a fragrant material. Without unfavourable changes of fragrant material, occurring in the preparation of the fragrance, such as volatile emission, spoilage, discoloration and foreign odor development, there is provided a gel-like fragrance composition allowing the fragrance selection spectrum to be widened, with excellent lasting deodorant effect and fragrant balance, and in particular with good durability of the fragrance at latter stages of use.

10 Claims, No Drawings

GEL-LIKE FRAGRANCE COMPOSITION

BACKGROUND OF THE INVENTION

1. Field of the Invention

The present invention relates to a gel-like fragrance composition, in particular such composition with good volatilisation-control property.

2. Description of the Prior Art

Conventionally, gel-like fragrance compositions have been used in order to solidify fragrant fluid materials, to control the degree of volatilisation, and to provide a good appearance due to mouldability and transparency. Gel-like fragrance compositions are roughly divided into two categories, i.e. an aqueous gel-like and an oilly gel-like. Of the aqueous gel-like, the aroma component-containing oil phase is emulsified in a water phase containing natural aqueous gelling agents, such as agar and carragennan (JP-A-54-135229) and the like, or synthesised gelling agents, such as a water-soluble polymer (JP-A-55-81655) and the like. Of the oilly gel-like, those prepared in that an aroma component is solubilised in an oil phase containing oilly gelling agents, such as higher fatty acid soap, in particular sodium stearate (U.S. Pat. No. 4,117,110), dibenzylidene sorbitol (JP-A-59-77859) and the like; and those in which an oil-absorbable resin (EP-A-0 441 512) is employed.

Recently, the design of fragrance products has become of considerable interest in connection with domestic environment equipment and consumers' preferences, and it is also seen that many such products are applied to fashionable goods. However, for product to be fragrant, it is still necessary to select the quality and kind of the aroma as the most important features. The development of fragrance bases and volatile emission systems aiming at the following effects as fragrance is desired: no changes in the constant volatile emission; good quality of scent; sufficient fragrance strength; and a defined terminating point.

In view of the nature of the goods, it is required that the aroma be constant over a long period without deterioration. On the other hand, concerning fragrance bases of the spray, liquid, solid or gel and the like, seen in the current market, the aromatic components are emitted by volatilisation starting with the lower boiling point components. If the emitted aroma components are not compensated for, the tone balance is lost over the time, and simultaneously the aroma becomes weak. Accordingly, it was impossible to maintain a fixed fragrance tone for a long time.

In order to achieve a well-balanced volatile emission, there is employed the technique of controlling changes of the scent by incorporation of solvents with high boiling points, so-called fixatives, or of using high boiling point fragrant materials, Although this technique may constitute a basis for the preparation of scents durable over prolonged periods of time, it is nevertheless insufficient to control the volatile emission velocity difference between the fragrant substances of a multi-component mixture completely. In oil type fragrant materials bases dispersed in aqueous systems, the balance between surfactants amount and aroma is restricted, generally due to the use of limonene or the like contributing to the "fresh note", the incorporation amount of terpens (being rapidly volatile) being also restricted, so that a defined product life span is not attainable.

Accordingly, an object of the present invention is to provide a nobel gel-like fragrance composition. Another object of the present invention is to provide a convenient, gel-like fragrance composition excellent in the economic performance with improved release control in respect of scents, in view of the requirements concerning a "retarded release of a well-balance scent", a "consistent scent emission from beginning to end throughout", a "lasting of fresh note" and a "defined terminating point". Still another of the present invention is to provide a gel-like fragrance composition which widens the perfume selection spectrum, with control of the alternations in scent emission over the time, simulteneously having a defined terminating point.

SUMMARY OF THE PRESENT INVENTION

These objects can be attained by a gel-like fragrance compositions which comprises an aqueous gel comprising an aqueous fluid and a gelling agent incorporated an oil-absorbable resin (II) carrying a fragrant material.

Without unfavourable changes, such as changes in volatile emission, deterioration, discoloration and foreign odour development of fragrant material, which tend to arise in the preparation of fragrance products,there is provided a gel-like fragrance compositions, the present invention allowing such gel-like fragrance composition to exhibit a widened fragrance selection spectrum, with excellent lasting fragrancy and deodorant effect, and well-balanced aroma, and in particular with good durability of the fragrance during the later period of use.

In consideration of said excellent properties, the present gel-like fragrance compositions are useful in a broad field, e.g. as domestic fragrant deodorants in vehicle's indoors, in toilets, in bathrooms, in living rooms, and as multi-purpose fragrance products for admixing with pharmaceuticals and pesticides.

EXPLANATION OF THE PREFERRED EMBODIMENT

The oil-absorbable resin (II) used in the present invention is not particularly limited as far they are capable of absorbing and carrying fragrant materials. They are, e.g., polynorbornene rubber and hydrophobic cross-linked polymers, preferably cross-linked polymers comprising 90 to 99.999% by weight of a monofunctional monomer component (A) mainly comprising an unsaturated monomer having not more than 9 of a solubility parameter and at least one polymerizable unsaturated group in the molecule, and 0.001 to 10% by weight of a cross-linkable monomer component (B) having at least two polymerizable unsaturated groups or reactive substituents in the molecule.

The solubility parameter (SP value) is commonly used as a measurement value representing the polarity of the compound. In the present context, Hoy's cohesive energy constant is applied to Small's formula, the resulting number being represented by units $(cal/cm^3)^{1/2}$.

The monomers forming the main component of the monomer (A) employed in the preparation of the oil-absorbable resin (II) are monomers with an SP value of not more than 9, having one polymerizable unsaturated group in the molecule. The use of monomers with an SP value exceeding 9 as the main component of monomer (A) is not favourable since only cross-linked polymers with insufficient oil absorbency of this type are available.

Monomers having the SP value of not more than 9 and having at least one polymerizable unsaturated group are unsaturated carboxylic acid esters such as methyl-(meth)acrylate, ethyl(meth)acrylate, butyl(meth)acrylate, t-butyl(meth)acrylate, 2-ethylhexyl(meth)acrylate, n-octyl-(meth)acrylate, dodecyl(meth)acrylate, stearyl(meth)acrylate, phenyl(meth)acrylate, octylphenyl(meth)acrylate, nonylphenyl(meth)acrylate, dinonylphenyl(meth)acrylate, cyclohexyl(meth)acrylate, menthyl(meth)acrylate, isobornyl(meth)acrylate, dibutylmaleate, didodecylmaleate, dodecylcrontonate, didodecylitoconate; (meth)acryliamides having hydrocarbon groups such as (di)butyl(meth)acrylamide, (di)dodecyl(meth)acryliamide, (di)stearyl(meth)acryliamide, (di)butylphenyl(meth)acryliamide, (di)octylphenyl(meth)acryliamide and the like, α-olefines such as 1-hexene, 1-octene, isooctene, 1-nonene, 1-decene, 1-dodecene and the like; cycloaliphatic vinyl compounds such as vinylcyclohexane and the like; allyl ethers having hydrocarbon group such as dodecylallylether and the like; vinyl esters having hydrocobon group such as vinyl caproate, vinyl alurate, vinyl palmitate, vinyl stearate and the like; vinyl ethers having hydrocobon group such as butylvinyl ether, dodecylvinyl ether and the like; aromatic vinyl compounds such as styrene, t-butylstyrene, octylstyrene and the like; and one or more of these monomers may be used.

Among these monomers, those imparting particularly excellent oil-absorbancy and oil-retaining ability, i.e. monomers (A) mainly comprising at least one unsaturated compound (a) having at least one aliphatic hydrocarbon group of 3 to 30 carbons, preferably to and selected from the group consisting of alkyl(meth)acrylate, alkylaryl(meth)acrylate, alkyl(meth)acrylamide, alkylaryl(meth)acrylamide, fatty acid vinyl ester, alkylstyrene and α-olefines, are particularly preferable.

The proportional amount of incorporation of such monomers with an SP value of not more than 9 in the monomer (A) is not less than 50% by weight, preferably not less than 70% by weight, based on the total amount of monomer (A). In case the amount is less than 50% by weight, only resins inferior in oil absorption and oil retention are obtainable.

Therefore, in the present context, it is required that not less than 50% of the monomer with an SP value of not more than 9 be incorporated with the monomer (A) component. Monomers with an SP value exceeding 9, containing one polymerizable unsaturated group in the molecule, may be incorporated in a proportional amount of not more than 50% by weight with the monomers (A). Such monomers are e.g. (meth)acrylic acid, acrylonitrile, maleic anhydride, fumaric acid, hydroxyethyl (meth)acrylate, polyethyleneglycol (meth)acrylate, methoxy polyethyleneglycol (meth)acrylate, and the like.

Examples of the present cross-linkable monomers (B) are, e.g., ethyleneglycol di(meth)acrylate, diethyleneglycol di(meth)acrylate, polyethyleneglycol di(meth)acrylate, polyethyleneglycol-polypropylene glycol di(meth)acrylate, polypropyleneglycol di(meth)acrylate, polypropylene glycol di(meth)acrylate, 1,3-butyleneglycol di(meth)acrylate, neopentylglycol di(meth)acrylate, 1,6-hexanediol di(meth)acrylate, N,N'- methylenebisacrylamide, N,N'-propylenebisacrylamide, glycerol tri(meth)acrylate, trimethylolpropane tri(meth)acrylate, tetramethylolmethane tetra(meth)acrylate, polyfunctional (meth)acrylates obtainable from esterifying between alkylene oxide addition product of polyalcohol (such as glycerol, trimethylolpropane or tetramethylolmethane) and (meth)acrylic acid, divinylbenzene and the like; and one or more of these cross-linkable monomers may be used.

The proportion of the monomer components (A) and (B) used in the preparation of the present oil-absorbable resin (II) is 90 to 99.999% by weight, preferably 96 to 99.999% by weight for monomer component (A) and 0.001 to 10% by weight, preferably 0.001 to 4% by weight for the cross-linkable monomer component (B), based on the total of (A) and (B).

If the component (A) amounts to less than 90% by weight, i.e. the cross-linkable component (B) exceeds 10% by weight, the obtained cross-linking density of the cross-linked polymer is too high and absorption of larger amounts of fragrant materials becomes impossible, this being undersireble.

It is preferred that the oil-absorbable resin (II) in the present invention is used in particle state. The particles can be prepared in that e.g., said monomer components are dispersed in an aqueous medium in the presence of a protective colloid agent such as polyvinyl alcohol, hydroxyethyl cellulose, gelatine, or of surfactants such as sodium alkyl sulphonate, sodium alkylbenzenesulphonate, polyoxyethylenealkyl ether, aliphatic acid soap, and suspension polymerization is effected with an oil-soluble radical polymerization initiator. If necessary, it is also possible to dissolve the monomer components first in a water-insoluble organic solvent, whereafter suspension polymerization is carried out. By such suspension polymerization, an aqueous dispersion of oil-absorbable resin (II) particles is obtained, this aqueous dispersion being suitable for mixing with an aqueous gel (I), and subjected to treatment in a granulation step.

Furthermore, this aqueous dispersion of the oil-absorbable resin (II) particles may be further granulated and the granulated aqueous dispersion utilised for mixing with an aqueous gel (I) and subjection to a gelling step. Further, the granulated particles may be filtered, dried, and then subjected to a gelling step.

The oil-soluble radical polymerization initiators are, e.g., organic peroxides, such as benzoyl peroxide, lauroyl peroxide, cumenehydroperoxide and the like; or azo compounds, such as 2,2'-azobisisobutylonitrile, 2,2'-azobisdimethyl valeronitrile and the like. The polymerization temperature can be suitably selected in the range of 0° to 150° C., preferably 40° to 100° C., depending on the kinds of monomer components and polymerization initiator.

Another possible way of particles preparation is that in which bulk polymerization is effected in order to polymerise an oil-absorbable resin (II), whereafter crushing is effected in order to regulate the particle size. Bulk polymerization is effected, e.g., as follows: The monomer components are poured into a mould in the presence of said polymerization initiator, and polymerization is conducted at 50° to 150° C., preferably 50° to 120° C.

In the present preparation procedure, the kinetic power exerted by stirring and the granulation conditions during the polymerization are controlled so as to produce particles with an average particle size of 0.5 to 5000 μm, especially 10 to 3000 μm. An oil-absorbable resin (II) with an average particle size less than 0.5 μm exhibits flocculation of particles, which hinders absorption and support of fragrant material. An oil-absorbable resin (II) having an average particle size exceeding 5000 μm exhibits a volatile emission which is not controllable in accordance with the decrease in resin surface area and thus not favourably.

In the preparation of the present aqueous gel (I), an aqueous liquid and a gelling agent suitable for homogenisation and gelling of the aqueous liquid are employed.

The aqueous liquid may be one comprising water as main component, but mixtures of organic solvents miscible with water, such as alcohols, containing water are also suitable. The surfactants, fragrant materials and the like can be dissolved or dispersed in the aqueous liquid in an amount which does not hinder gelling of the aqueous gel (I).

As far as capable of aqueous gel formation, the gelling agents used are not particularly limited. Animal polymeric compounds, such as glue gelatine, collagen protein, chondroitin acids sodium salt, casein, and the like; vegetable polymeric compounds, such as pectin calcium salt, pectin aluminium salt, agar, alginic acid Furcellaran, pectin, Tamarindseed oligosaccharides, gum arabic, guar gum, tragacanth gum, Locust bean (*Ceratonia siliqua*) gum, Xanthan gum, carageenan, modified starch, cyclodextrin and the like; cellulose series water-soluble macromolecules such as carboxymethyl cellulose, hydroxymethyl cellulose, hydroxypropylmethyl cellulose, carboxyl cellulose, nitrate phthalate cellulose; synthetic water-soluble macromolecules such as polyethyleneimine, polyvinylalcohol, sodium polyacrylate, cross-linked acrylate polymers and the like; and thermosetting or UV-setting resins, such as urethane resin and epoxy resin and the like; singly or in combination can be employed.

The present gel-like fragrance composition composed of an oil-absorbable resin (II) carrying fragrant material is incorporated with an aqueous gel (I).

The method for carrying the fragrant material onto the oil-absorbable resin (II) is not particularly limited, i.e. any of the following ways is suitable: Mixing of the oil-absorbable resin (II) particles with the fragrant material so that the material is adsorbed and supported; Dispersion of the fragrant material is and mixing thereof into the aqueous dispersion of such particles so that the fragrant material is adsorbed by and supported on the particles; As far as possible under avoidance of deterioration of the fragrant material, heating of the fragrant material in order to accelerate the velocity of absorption by the oil-absorbable resin (II).

The fragrant material amount carried by the oil-absorbable resin (II) is not particularly limited as long as it is completely absorbed by the oil-absorbable resin (II).

The fragrant materials used according to the present invention are obtainable by optional formulation of the following substances: monoterpens such as limonene; diterpens such as abietin; terpenic alcohols such as linalool; alcohols such as benzyl alcohol; terpenic aldehydes such as citral; terpenic kotones such as menthone; aromatic ketones such as p-methyl acetophenone; phenol derivatives such as diphenyl ether; aromatic hydrocarbons such as p-cymene; aliphatic aldehydes such as decanal; aromatic aldehydes such as benzaldehyde; acetals such as citral dimethyl acetal; carboxylate esters such as isoamyl acetate; aliphatic cyclic ketones such as $\alpha,\beta,\gamma$-ionone; macrocyclic ketones such as muscone; cyclic ethers such as rose oxide; heterocyclic compounds such as indole; esters of aliphatic acid such as geranyl formate; esters of aromatic acids such as methyl benzoate; and aldehydes such as $\gamma$-heptyl butyrolactone.

In addition, diluting fillers for fragrant material, such as isoparaffins, isopropyl myristate and the like which are fluid and volatile at normal temperature, are employable when mixed with the fragrant material. Furthermore, if necessary, additives, such as antioxidants (e.g. BHT and the like), pigments, pesticides, or pharmaceuticals may be incorporated.

A fragrant material which is identical or not identical with the fragrant material supported by the oil-absorbable resin (II) and surfactants may be contained in the aqueous gel (I). By dispensation of fragrant material in both the oil-absorbable resin (II) and the aqueous gel (I), the release delay effect is improved, and control of the aroma change with the time is attained.

An amount of the fragrant material to be supported to the oil-absorbable resin (II) is in the range of 10 to 3000% by weight, preferably 300 to 2000% by weight. An amount of the fragrant material to be contained in the aqueous gel (I) is in the range of 0 to 20% by weight, preferably 1 to 10% by weight, and an amount of the surfactant is in the range of 0 to 20% by weight, preferably 0 to 10% by weight. Further, ratio of the aqueous gel (I) to the oil-absorbable resin (II) is 1:99 to 99.99:0.01, preferably 10:90 to 99.9:0.1 % by weight ratio.

The surfactants employed in order to solubilise the fragrant material or to disperse them in the aqueous liquid are not particularly limited as long as they are capable of uniformly dispersing both components. Therefore, any dispersion agent of the anionic, cationic and nonionic surfactant series, water-soluble macromolecules, and the like are suitable.

Such surfactants are, for instance, anionic surfactants: such as carboxylic acid salts, e.g. aliphatic monocarboxylates, abietinate and the like, sulphonic acid salts e.g. dialkyl sulphosuccinate, linear alkyl benzene sulphonate, sodium N-methyl-N-oleyl taurate and the like, sulphuric acid ester salts e.g. alkyl sulphuric acid ester salt, polyoxyethylene alkylphenyl ether sulphuric acid ester and the like, phosphoric acid ester salts e.g. alkyl phosphoric acid ester salt, polyoxyethylene alkyl phenylether phosphoric acid ester salt and the like, anionic polymerization type polymer e.g. partial oxide of styrene maleic anhydride copolymer and the like, anionic polycondensation type polymers e.g. naphthalenesulphonic acid salt-formalin condensation product and the like; cationic surfactants: such as primary, secondary or tertiary amine salts of alkyl amine, dialkyl amine and the like, quaternary ammonium salts e.g. tetraalkylammonium salts and the like, polytheylene polyamine derivatives e.g. polyethylene polyamine aliphatic acid amide salt and the like; ether type non-ionic surfactants such as polyoxyethylene alkylether, polyoxyethylene alkyl phenylether, polyoxyethylene polyoxypropyrene glycol and the like; ester type non-ionic surfactants such as polyoxyethylene alkylether, polyoxyethylene alkyl phenylether, polyoxyethylene polyoxypropyrene glycol and the like; ester type non-ionic surfactants such as glyceric aliphatic acid partial ester, sorbitan aliphatic acid partial ester; ester ether type non-ionic surfactants such as polyoxythylene sorbitan aliphatic acid partial ester, polyethylene glycol aliphatic acid ester and the like; nitrogen-containing type non-ionic surfactants such as aliphatic acid diethanol amide and the like; ampholytic surfactants of carboxy betaine type, amino carboxylic type, sulphobetaine type, amino sulphuric acid ester type, imidazoline type and the like; water-soluble polymers such as: synthetic polymers such as polyvinyl alcohol, sodium polyacrylate, polyethylene oxide and the like; natural macromolecules such as cellulose derivatives e.g. carboxymethyl cellulose, methyl cellulose, hydroxyethyl cellulose and the like, resin polysaccharides, vegetable seed polysaccharides, seaweed polysaccharides, pectin, starch, fermentation polysuccharides by microorganisms, proteins and the like; employed eparately or in combination.

The gelling procedure in the preparation of the present gel-like fragrance composition is not particularly limited as long as it results in the formation of an aqueous gel. The gelling may be effected in the following way: Gelling agents, if necessary, and surfactants are dissolved in an aqueous liquid, the fragrant material is likewise solubilised or dispersed in the aqueous liquid, the oil-absorbable resin (II) to support the fragrant material is further mixed in, and the mixture is cooled or heated to the gelling temperature, or an auxiliary gelling agent is incorporated.

In addition, colorants, preservatives, antioxidants, various fillers for improvement of the appearance such as flowers, petals, and coloured materials, reflecting materials, etc. may be incorporated with this aqueous gel.

Hereinafter, the invention is illustrated by way of Examples in a non-limiting way, all parts being by weight unless otherwise stated.

REFERENCE EXAMPLE 1

Into a 500 ml flask with a thermometer, stirrer, gas introduction tube and reflux condenser, 3 parts of polyoxyethylene alkyl ether (SOFTANOL 15, manufactured by Nippon Shokubai Co., Ltd.) dissolved in 300 parts of water were charged, nitrogen-substitution within the flask was effected under stirring, and the solution was heated to 40° C. under nitrogen gas flow. Thereafter, a solution comprising 59.762 parts of isobutyl methacrylate (SP value: 8.7) and 39.841 parts of stearyl acrylate as monomer (A), 0.396 part of 1,6-hexanediol diacrylate as cross-linkable monomer (B), and 0.5 part of benzoyl peroxide as polymerization initiator was introduced into the flask all at once, and the content was stirred at 300 r.p.m.

Subsequently, the temperature inside flask rose to 80° C., and this temperature was maintained for 2 hours in order to effect polymerization. Thereafter, the temperature inside the flask was raised to 90° C. and this temperature maintained for 2 hours whereby the polymerization was completed, so that an aqueous dispersion (pure resin content: 25%) containing an oil-absorbable polymer (1) with an average particle size of 300 μm was obtained. Filtration, drying and pulverisation of this aqueous dispersion yielded an oil-absorbable resin (1).

REFERENCE EXAMPLE 2

A procedure analogous to that in Reference Example 1 was carried out except that 1 part of linear sodium alkyl (carbon number: 12 to 13) benzene sulphonate instead of the polyoxyethylene alkyl ether in Reference Example 1; 99.823 parts of dodecyl acrylate (SP value: 7.9) as monomer (A); and 0.177 parts of ethylene glycol diacrylate as cross-linkable monomer (B) were used; and that a 450 r.p.m. stirrer rotation speed was employed in the polymerization. An aqueous dispersion (pure resin content: 25% by weight) containing an oil-absorbable cross-linked polymer (2) with average particle size of 30 μm was abtained. Filtration, drying and pulverisation of this aqueous dispersion yielded an oil-absorbable resin (2).

REFERENCE EXAMPLE 3

A procedure analogous to that in Reference Example 1 was carried out except that 59.878 parts of t-butyl styrene (SP value: 7.9) and 39.919 parts of vinyl laurate (SP value: 7.9) as monomers (A); and 0.203 part of divinyl benzene as cross-linkable monomer (B) were used instead. An aqueous dispersion (pure resin content: 25% by weight) containing an oil-absorbable cross-linked polymer (3) with an average particle size of 300 μm was obtained. Filtration, drying and pulverisation of this aqueous dispersion yielded an oil-absorbable resin (3).

REFERENCE EXAMPLE 4

Into a glass mould for casting and polymerization with a thermometer and a gas introduction tube (a tray of 5×5×1 cm size), a mixed solution comprising 49.930 parts of hexadecyl methacrylate (SP value: 7.8) and 49.930 parts of N-cotyl methacryl amide (SP value: 8.6) as monomers (A), 0.140 part of divinyl benzene as cross-linkable monomer (B), and 0.1 part of 2,2'-azobisdimethyl valeronitrile as polymerization initiator was introduced. The mixture was heated under nitrogen gas flow at 60° C. for 2 hours in order to effect polymerization, whereafter the temperature was raised to 80° C. and maintained there for 2 hours in order to complete the polymerization. The reaction liquid was left to cool, then the gel product was released from the mould, and pulverization of the gel gave an oil-absorbable resin (4).

EXAMPLE 1

91.6 g of water were weighed into a 200 ml cup, and 2.4 g gelling agent (λ-carrageenan, guaranteed reagent, manufactured by Junsei Kagaku K.K.) were gradually incorporated under stirring in order to dissolve. Subsequently, the cup was put into a warm bath of 80° C., 0.1 g of preservative (Poxel BDN, manufactured by ICI) and 0.2 g of gelling enforcement agent (potassium chloride) were added thereto, the mixture was heated until the inside temperature of 75° C. was reached under stirring, and when the temperature had reached at 75° C., stirring was continued for 10 minutes. The cup was then taken out of the warm bath, cooled under stirring to 55° C., a previously prepared mixture composed of 4 g of citrus series fragrant material (Lemon SW 93 025 B, manufactured by Nihon Firmenich K.K.), mainly comprising limonene, citral and linalool, 0.5 g of wetting agent (dipropylene glycol), a trace of water-soluble dye, and 0.2 g of surfactant (RHEODOL MS-60, manufactured by Kao Corporation) were incorporated therewith, and the mixture was cooled to 43° C. under stirring.

An oil-absorbable resin (1) carrying a fragrant material had been prepared in the following way: 0.1 g of oil-absorbable resin (1) and 0.9 g natural essence oil fragrant material (Orange Terpens CP 1100 ARR, manufactured by Nihon Firmenich K.K.), mainly comprising limonene, were mixed at normal temperature so that the fragrant material became completely absorbed. 1 g of this oil-absorbable resin (1) carrying fragrant material was added to the above mixture the whole, stirred well and quickly cooled in a refrigerator in order to provide a gel-like fragrance composition (1).

EXAMPLE 2

44.0 g of water and 5 g of 5% aqueous citric acid solution were weighed into a 200 ml of cup, 1g gelling agent (HIVSWAKO 105, manufactured by Wako Pure Chemical Industries, Ltd.) was gradually added thereto under stirring, and the mixture heated to 75° C. for dissolution. After cooling to room temperature, a mixture composed of 5 g fragrant material (ROSE SW 93 027, manufactured by Nihon Firmenich K.K.), 0.8 g of surfactants (HCO-50, manufactured by Nikko Chemical K.K.), 0.2 g of (NP-10, manufactured by Nikko Chemical K.K.) and a trace of dye was added and the whoule well stirred.

An oil-absorbable resin (2) carrying a fragrant material had been prepared by following way: 0.1 g of oil-absorbable resin (2) and 0.9 g fragrant material (Orange Terpens CP 1100 ARR, manufactured by Nihon Firmenich K.K.) were mixed at normal temperature so that the fragrant material became completely adsorbed. 1 g of this oil-absorbable resin (2) carrying fragrant material was added to the above mixture, the mixture was well stirred, and neutralisation by way of incorporation of 3 g 10% 2-aminoethanol in ethanol solution (95%, manufactured by Wako Pure Chemical Industries, Ltd.) flashingly yielded a transparent gel-like fragrance composition (2).

EXAMPLE 3

64.8 g of water were weighed into a 200 ml of cup, 4 g of green apple tone fragrant material (Green Apple 136.660, manufactured by Nihon Firmenich K.K.), 5 g, of surfactant (NP-10, manufactured by Nikko Chemical K.K.), 7 g of ethanol as auxiliary for fragrant material solubilisation, and 7 g of dipropylene glycol as viscosity modifier were incorporated therewith, and the whole was stirred.

Thereafter, 0.1 g sodium sulphate as stabiliser, 0.1 g UV-absorbent 2-hydroxy-4-octoxy benzophenone (Sumisoap 130, manufactured by Sumitomo Chemical Co., Ltd.) and a trace of dye were added, the whole was well stirred, and further 10 g of urethane resin type gelling agent (C-2020, manufactured by Mitsubishi Petrochemical Co., Ltd.) were added. Subsequently, 1 g of oil-absorbable resin (3) carrying a fragrant material, which had been prepared in the following way, was added thereto: 0.9 g of fruity tone fragrant material (Furuity 136.077, manufactured by Nihon Firmenich K.K.), mainly comprising Allyle Caprote, was admixed with 0.1 g of oil-absorbable resin (3) at normal temperature so that the fragrant material became completely adsorbed. The mixture was well stirred to become homogenised, and left to stand at normal temperature for 10 to 20 minutes in order to provide gel-like fragrance composition.

EXAMPLE 4

3 g of natural hectorite and 94.0 g of water were weighed into a 200 ml of cup, and a trace of water-soluble dye was added thereto.

Then, 3 g oil-absorbable resin (4) carrying a fragrant material, which had been prepared in the following way: 0.3 g oil-absorbable resin (4) and 2.7 g fragrant material (Orange Terpens CP 1100 ARR, manufactured by Nihon Firmenich K.K.) were admixed at normal temperature so that the fragrant material became completely adsorbed; was added the above mixture. The mixture was well stirred and gelled under stirring in order to provide gel-like fragrance composition (4).

CONTROL 1

Except for the direct incorporation of 0.9 g of natural essence fragrant material (Orange Terpens CP 1100 ARR, manufactured by Nihon Firmenich K.K.), mainly comprising limonene, into the aqueous solution instead of the use of an oil-absorbable resin (1) according to Example 1, the same procedure as in the Example 1 was carried out and gave a gel-like fragrance composition (1) for comparison.

CONTROL 2

Except for the direct incorporation of 0.9 g of natural essence fragrant material (Orange Terpens CP 1100 ARR, manufactured by Nihon Firmenich K.K.) mainly comprising limonene into the aqueous solution instead of the use of an oil-absorbable resin (2) according to Example 2, the same procedure as in Example 2 was carried out and gave a gel-like fragrance composition (2) for comparison.

CONTROL 3

Except for the direct incorporation of 0.9 g of fruity tone fragrant material (Furuity 136.077, manufactured by Nihon Firmenich K.K.) mainly comprising Allyle Caprote, into the aqueous solution, instead of use of an oil-absorbable resin (3) according to Example 3, the same procedure as in Example 3 gave a comparison gel-like fragrance composition (3).

EXAMPLE 5

In respect of the gel-like fragrance compositions (1) to (4) according to the present Examples 1 to 4 and comparative gel-like fragrance compositions (1) to (3) according to Controls 1 to 3, a volatile emission evaluation by way of weight change determination and a panel test by selected panel members were carried out in the following way.

Volatile Emission Evaluation

For a period of time matching the practical application period of gel-like fragrance compositions, the compositions were left to stand in the open air at room temperature. Evaluation was made in % by weight of "after application" against "before application".

Panel Test

For a period of time matching the practical application period of the gel-like fragrance compositions, the compositions were left to stand in the open air at room temperature. Thereafter the compositions were left to stand in a 200 l drum for 15 minutes, and the 5-membered panel organoleptically judged the fragrance strength emitted within the drum by the following evaluation grading:

Fragrance strength:

Power 1, extremely strong; Power 2, rather weak; Power 3, suitable as fragrance; Power 4, rather strong; Power 6, too strong.

The results of the volatile emission evaluation of the panel aroma testa are listed in TABLE 1.

TABLE 1

| | | Evaluation of the volatile emission, and results of the panel test | | | | | |
|---|---|---|---|---|---|---|---|
| | | Initial point | 1 week | 2 weeks | 3 weeks | 4 weeks | 5 weeks |
| Example 1 | Weight change | 100 | 70 | 54 | 38 | 24 | 13 |
| | Organoleptic strength | 5 | 5 | 4 | 4 | 3 | 2 |
| Example 2 | Weight change | 100 | 61 | 42 | 23 | 18 | 14 |

TABLE 1-continued

Evaluation of the volatile emission, and results of the panel test

|  |  | Initial point | 1 week | 2 weeks | 3 weeks | 4 weeks | 5 weeks |
|---|---|---|---|---|---|---|---|
| Example 3 | Organoleptic strength | 5 | 5 | 4 | 4 | 3 | 2 |
|  | Weight change | 100 | 77 | 62 | 48 | 32 | 29 |
| Example 4 | Organoleptic strength | 5 | 5 | 4 | 4 | 3 | 3 |
|  | Weight change | 100 | 58 | 40 | 27 | 15 | 10 |
| Control 1 | Organoleptic strength | 5 | 5 | 4 | 4 | 3 | 2 |
|  | Weight change | 100 | 68 | 53 | 37 | 22 | 11 |
| Control 2 | Organoleptic strength | 5 | 4 | 3 | 2 | 2 | 1 |
|  | Weight change | 100 | 58 | 48 | 21 | 16 | 14 |
| Control 3 | Organoleptic strength | 5 | 3 | 3 | 2 | 1 | 1 |
|  | Weight change | 100 | 76 | 60 | 48 | 31 | 29 |
|  | Organoleptic strength | 5 | 4 | 4 | 3 | 3 | 2 |

What is claimed is:

1. A gel-like fragrance composition which comprises:
   an aqueous gel comprising an aqueous fluid and a gelling agent; and
   an oil-absorbent resin having absorbed a fragrant material; wherein said oil-absorbent resin is a cross-linked polymer comprising 90 to 99.999% by weight of a monofunctional monomer component mainly comprising an unsaturated monomer having a solubility parameter of not more than 9 and at least one polymerizable unsaturated group in the molecule, and 0.001 to 10% by weight of a cross-linkable monomer component having at least two polymerizable unsaturated groups or reactive substituents in the molecule; and wherein said oil-absorbent resin is dispersed in said aqueous gel.

2. A composition according to claim 1, wherein said aqueous gel containes at least one fragrance selected from the group consisting of fragrances of the same kind as carried on said oil-absorbent resin and other kinds of fragrances and a surfactant.

3. A composition according to claim 1 or 2, wherein the amount of said polymerizable monomer having a solubility parameter of not more than 9 in said monofunctional monomer is not less than 50% by weight of the whole amount of said monofunctional monomer.

4. A composition according to claim 3, wherein said polymerizable monomer having a solubility parameter of not more than 9 is at least one unsaturated compound selected from the group consisting of alkyl (meth)acrylates, alkyl aryl(meth)acrylates, alkyl (meth)acrylamides, alkyl aryl(meth)acrylamides, fatty acid vinyl esters, alkyl styrenes, and α-olefines severally having an aliphatic hydrocarbon group of 3 to 30 atoms.

5. A composition according to claim 1, wherein said oil-absorbent resin is in a particulate form.

6. A composition according to claim 5, wherein said particulate oil-absorbent resin is obtained by dispersing said monomer components in an aqueous medium in the presence of a protective colloidal agent or a surfactant and suspension polymerizing the resultant dispersion by use of an oil-soluble radical polymerization initiator.

7. A composition according to claim 3, wherein said particulate oil-absorbent resin is obtained by pulverizing said oil-absorbent resin and then subjecting the pulverized resin to adjustment of grain size.

8. A composition according to any of claims 3 to 7, wherein said particulate oil-absorbent resin has an average particle diameter in the range of from 0.5 to 5,000 μm.

9. A composition according to any of claims 1 to 2 and 5 to 7, wherein the ratio of said aqueous gel to said oil-absorbent resin is in the range of from 1:99 to 99.99:0.01 by weight.

10. A composition according to any of claims 1 to 2 and 5 to 7, wherein the amount of said fragrance carried on said oil-absorbent resin is in the range of from 10 to 300% by weight based on the amount of said oil-absorbent resin.

* * * * *